United States Patent [19]

Chang et al.

[11] 4,082,918

[45] Apr. 4, 1978

[54] AUDIO ANALGESIC UNIT

[76] Inventors: Roland Wan-chan Chang, 17700 NW. 12 Ave., Miami, Fla. 33169; Charles A. Graves, 251 E. Park Ave., Lake Wales, Fla. 33853

[21] Appl. No.: 760,838

[22] Filed: Jan. 21, 1977

[51] Int. Cl.² ........................ A61B 19/00; A61N 1/00
[52] U.S. Cl. .................................................. 179/1 AA
[58] Field of Search .................. 179/1 AA; 128/1 R

[56] References Cited
U.S. PATENT DOCUMENTS 2,986,140  5/1961  Gardner ............................... 128/1 R
3,213,851  10/1965  Currea ............................... 179/1 AA Primary Examiner—Kathleen H. Claffy
Assistant Examiner—E. S. Kemeny

[57] ABSTRACT

An audio analgesic unit for use in masking sounds and substituting another sound which includes earmuffs to be used by a dental patient in which speakers are arranged and connected to a patient operated remote control unit to control the sound levels and a master control unit to override the patient remote control unit and operated by an operator, such as a dentist. A beeper indicates operation mode change.

2 Claims, 1 Drawing Figure

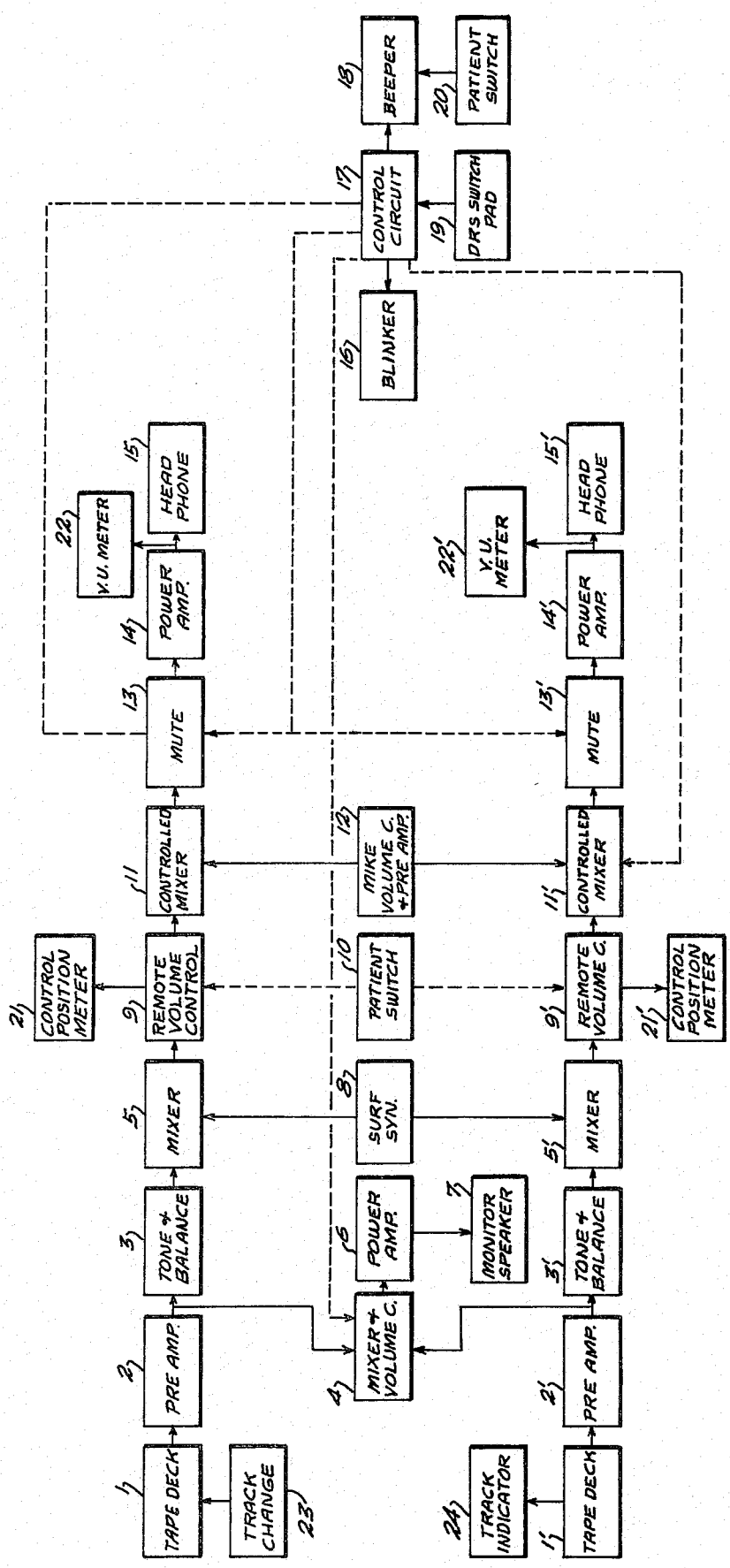

AUDIO ANALGESIC UNIT

FIELD OF THE INVENTION

This invention relates to an audio analgesic device.

BACKGROUND OF THE INVENTION

As is perhaps well known, many sounds that a patient hears while being treated by a doctor are nerve-racking. This invention is of a device which cuts out that sound by substituting through substantially sound proof earmuffs a substitute sound through a speaker connected in the earmuffs or headset which provides a relaxing type of music or other type of sound to a patient which masks disturbing sounds and yet which permits communication between the dentist and the patient in a manner in which is described herein. Representative prior art is to be found in U.S. Pat. No. 2,986,140.

OBJECTS OF THIS INVENTION

This invention is of a unit which has as an object means to relax a patient in the following manner.

The patient wears a headset which blocks out most sounds from the environment within which he is located. The headset includes earmuffs and a speaker arranged in the earmuffs. Through the headset speakers, the patient hears music, normally. The unit includes a microphone so that whenever the dentist wishes, he may speak into the microphone after depressing a switch, so as to override the patient's controls, described more fully hereinafter, so that the music volume is reduced or is interupted and the patient will hear the dentist or doctor speaking in the room. Selection of sounds may be made by the dentist either of music, or of a patterned sound, such as surf pounding on a rock, also known as modulated white noise. When the dentist shuts off the music and turns on the microphone so that he can communicate with the patient, a sound signal is emitted to alert him that this has been done and a light signal is also used so long as he speaks or has open communication with his patient. The patient is provided with a control unit to be hand-held which permits him to adjust the volume of the sound which he is hearing from his headset speakers and which also includes what is known as a "panic button" so that he can deprress it and signal to the doctor that he is experiencing pain or wishes to speak to him. The hand-held unit of the patient may also include a track change button so that he may change the tracks of the music he is listening to from a tape play deck which is connected to the speaker headphones.

DESCRIPTION OF THE DRAWINGS

The FIGURE is of a block diagram of the unit.

DESCRIPTION OF PREFERRED EMBODIMENT

Referring to the block diagram, the numeral 1 and 1' designate the tape deck transport mechanism means. Information is derived from the program source through the tape deck heads into blocks numbered 2 and 2'. Blocks numbered 2 and 2' are a tape deck preamplifier which amplifies the signal and changes the frequency response. The amplified signal splits after blocks 2 and 2' and a portion of both channels is fed into block numbered 4, which is a mixer and volume control, in order to change sound from a stereo source into monaural sound. The signal is from block 4 to block 6 which is a power or audio amplifier to amplify the sound to room listening volume. The signal goes from block 6 to block 7 which is a monitor speaker for the dentist so that the music which the patient is hearing in his headphone set can be heard by the dentist.

After the split the signal goes into blocks 3 and 3' which is a tone control, a balanced control, to balance the volume of the two channels, and also a manual volume control adjustable by the operator. This is a master control of the double pot type. From blocks 3 and 3' the signal goes into blocks 5 and 5' which is an electronic mixer. Block 5 is also fed by a synthetic surf generator 8. The surf generator is a modulated white noise generator, so tuned as to give the illusion of the sound of waves pounding in a pattern on rocks or a beach. Block 8 also contains a suitable volume control for the synthesizer. The volume controls for block 3 and 3' and for block 8 control the volume of the program source or of the synthesizer so the two can be mixed together in blocks 5 and 5' with each source level being independently adjustable. The signal leaves blocks 5 and 5' and goes into blocks 9 and 9' which are electronic attenuators for remote control operation.

The patient has a handpiece, block 10, with a control means for the volume, known in the art as a slave control for blocks 9 and 9'. The remote control switch is a digital type circuit and is fed from the switches in block 10 and controls the volume of the surf synthesizers and the program source only. The voice channel block numbered 12 contains means, known in the art, to amplify the microphone signal. Blocks 11 and 11' are controlled mixer units and are fed from blocks 9 and 9' and block 12. The control circuits, block 17, control blocks 11 and 11' so that, by the doctor depressing block 19, which is a switch pad, either foot-operated or finger-operated, or which may be both. Blocks 11 and 11' will switch signal sources from blocks 9 and 9' to block 12. If the unit is in a music mode, the block 12 is a microphone, a volume control for the microphone and a preamp. This allows communication from the doctor to the patient. Simultaneously block 18, the beeper, beeps three times. The blinker which is block 16 continues to blink until a switch block 19 is depressed.

When the switch is depressed, block 19 controls a block 17, and the control mixer block 11 mutes the microphone channel from block 12 and completes the path from the music channel. Block 16, the blinker means, then, ceases to blink and the beeper means beeps one time to indicate the return to the music mode. Blocks 13 and 13' are muting circuits so that any time block 19 is depressed, the signal in the microphones is completely muted if in the microphone mode or if in the music mode it will alternate the music sound level to a preset lower volume level. Block 17 is also a controlling factor on block number 4 which is a mixer and volume control for the monitor speaker.

Block 20 is a switch which is fed into block 18. If the patient experiences any discomfort or wishes to signal the dentist, he depresses this switch. When block 20 is depressed, feeding the circuit into block 18 causes a warning or warbling type sound. Block 23 is also on the patient control unit and is a switch which changes the tracks in the tape deck for different program material. Block number 24 gets its information from the tape deck and indicates what track is playing at the time.

The instant invention it will be seen uses a specifically modulated noise and the patient has a choice selecting that which he desires to hear, as does the dentist. This effectively masks disturbing sounds which the patient would otherwise hear, such as a dental patient, and this provides a means for controlling pain which the patient experiences because it has been found that, by so doing, the patent is more relaxed and his fear of pain is reduced.

What is claimed is:

1. Apparatus for relaxing a patient while being treated comprising:

a housing unit with an internal electronic circuit means and means to connect the circuit means to a source to energize it, first music signal means to generate a sound and including amplifier means, a first speaker for the dentist, said first speaker being connected to the first music signal means and said amplifier means, a set of earphones, each including speaker means to be worn by the patient and including means to connect to the first signal means and amplifier means, control means for the first speaker for the dentist to control the volume of the first speaker, hand-held control means for the patient to control the volume of the speaker means of the headset, a first beeper means on the unit, said apparatus also including switch means in series with the speaker means of said earphones to change the volume of music and signal to the earphones and to cause a signal from the beeper to indicate mode change.

2. The device as set forth in claim 1 wherein said apparatus includes control means for said first speaker.

* * * * *